(12) United States Patent
Ye

(10) Patent No.: US 9,913,530 B2
(45) Date of Patent: Mar. 13, 2018

(54) SMART TOOTHBRUSH

(71) Applicant: Hongzhao Ye, Dongguan (CN)

(72) Inventor: Hongzhao Ye, Dongguan (CN)

(73) Assignee: Hongzhao Ye, Dungguan (CN)

(*) Notice: Subject to any disclaimer, the term of this patent is extended or adjusted under 35 U.S.C. 154(b) by 10 days.

(21) Appl. No.: 15/152,435

(22) Filed: May 11, 2016

(65) Prior Publication Data

US 2016/0338484 A1    Nov. 24, 2016

(30) Foreign Application Priority Data

May 19, 2015  (CN) .......................... 2015 1 0255400
May 19, 2015  (CN) ..................... 2015 2 0323313 U

(51) Int. Cl.
| | | |
|---|---|---|
| *A46B 17/06* | (2006.01) | |
| *A61C 17/22* | (2006.01) | |
| *A46B 15/00* | (2006.01) | |
| *A46B 9/04* | (2006.01) | |

(52) U.S. Cl.
CPC ............... *A46B 17/06* (2013.01); *A46B 9/04* (2013.01); *A46B 15/0012* (2013.01); *A61C 17/221* (2013.01); *A61C 17/224* (2013.01); *A61C 17/225* (2013.01); *A46B 2200/1046* (2013.01)

(58) Field of Classification Search
CPC ....... A46B 17/06; A46B 9/04; A46B 15/0012; A61C 17/221; A61C 17/224; A61C 17/225
IPC ................................ A46B 17/06,9/04, 15/0012
See application file for complete search history.

(56) References Cited

U.S. PATENT DOCUMENTS

| | | | |
|---|---|---|---|
| 9,198,502 B2 * | 12/2015 | Barnes ...................... A46B 9/04 |
| 2016/0317007 A1 * | 11/2016 | Addington ............... A61B 1/24 |
| 2016/0331114 A1 * | 11/2016 | Follows .................. A61C 17/02 |
| 2016/0338635 A1 * | 11/2016 | Johnson ............... A61B 5/4547 |
| 2017/0020277 A1 * | 1/2017 | Barnes ................ A61C 17/3436 |
| 2017/0112603 A1 * | 4/2017 | Lee ..................... A61C 17/0208 |

* cited by examiner

*Primary Examiner* — Dung V Nguyen
(74) *Attorney, Agent, or Firm* — Timothy T. Wang; Ni, Wang & Massand, PLLC

(57) ABSTRACT

This disclosure provides a smart toothbrush, including a head, a front handle, a grip handle, a turning unit, a drying unit, a testing, unit, a power unit and a charge base. The front handle of the toothbrush using the disclosed device can revolve automatically by applying water on the bristles. The toothbrush resets automatically after being aired and dried for convenient and clean application for the next use.

20 Claims, 4 Drawing Sheets

SMART TOOTHBRUSH

TECHNICAL FIELD

This disclosure involves the technical field of articles for daily use, especially a smart toothbrush.

BACKGROUND TECHNOLOGIES

Toothbrushes are tools for dental cleaning in people's daily life. However, if toothbrushes themselves are not sufficiently clean, they will pose threat to the dental health of users. A toothbrush generally comprises a head and a handle. The head has bristles that are tightly lined. After users wash toothbrushes when they brush their teeth, toothbrushes often gather drops of water. Some users may throw drops of water out. Bristles may fail to dry timely so that they are often in a damp environment. As a result, it is highly easy for bristles to harbor bacteria, which is not favorable for dental health.

SUMMARY

In order to solve the problem of current technologies where bristles of toothbrushes gather drops of water, failing to dry timely and easily harboring bacteria, the device of the instant disclosure provides a smart toothbrush which makes it possible that after teeth brushing, bristles of the toothbrush can quickly dry to ensure dryness of bristles and reduce bacteria-harboring.

A smart toothbrush, including a head, a front handle and a grip handle. The head has bristles. The from handle and the grip handle of the toothbrush are connected by a rotating shaft.

The smart toothbrush has a rotating unit inside the front handle of the toothbrush, connected to the rotating shaft to control the rotating angle of the rotating shaft.

It also comprises a drying unit inside the groove below the grip handle of the toothbrush. A waterproof breathable film is set on the surface of the groove and it is linked to the exterior shell of the toothbrush in a leak-tight manner to dry the bristles of the toothbrush.

Additionally, the smart toothbrush comprises a testing unit inside the head of the toothbrush to test pressure. The testing unit includes a pressure sensor with a first pressure threshold and a second pressure threshold preset. The second pressure threshold is higher than the first pressure threshold. If a tested pressure ranges between the first pressure threshold and the second pressure threshold, a first rotating signal is send to the rotating unit. If the tested pressure is higher than the second pressure threshold, a second rotating signal is sent to the rotating unit. If the tested pressure is lower than the first pressure threshold, reset signal and stop-drying signals are sent to the rotating unit and drying unit simultaneously. A power unit is set on the top of the grip handle of the toothbrush and includes a battery and power switch. The power switch is set on the side of the grip handle of the toothbrush to supply power to the testing unit, drying unit and control unit. The rotating unit includes an angle sensor that receives the first rotating signal and controls the angle of rotating shaft to 45°, receives the second rotating signal and controls the angle of the rotating shaft to 30° to send drying signals to the drying unit after a corresponding angle value is achieved.

The drying unit includes a micro air blower that receives the drying signals and the micro air blower then begins blowing.

The rotating unit receives a reset signal to control the angle of the rotating shaft to rotate to 180° before sending circuit disconnection signals to the power unit.

The drying unit receives the stop-drying signal and the micro air blower then stops blowing.

The power unit receives a circuit disconnection signals to disconnect the power unit.

Compared with existing technologies, the beneficial effects of this disclosure may include a smart folding toothbrush, a micro air blower set inside a groove in the grip handle of the toothbrush wherein the surface of the groove is linked to an exterior shell of the toothbrush in leak-tight manner with waterproof breathable film. The micro air blower blows air out via this waterproof breathable film. Three angles may be set. A user may place the toothbrush onto the base after teeth brushing and the toothbrush rotates automatically based on current water volume of the toothbrush bristles. When the angle between bristles and the grip handle of the toothbrush is 45° and 30°, the micro air blower begins. The micro air blower may blow toothbrush bristles dry quickly to ensure the dryness of toothbrush bristles and reduction of bacteria and it may also enable the front handle of the toothbrush to be automatically reset to the working conditions of the toothbrush after blowing bristles dry for convenience of further use, simple and easy.

SPECIFIC EMBODIMENTS

In connection with the attached figures and the embodiment, embodiments of this disclosure are further specified below. It should be understood that the specific embodiment described hereof are simply designed for the purpose of interpreting the disclosure, instead of limiting, this disclosure.

Figure 1:
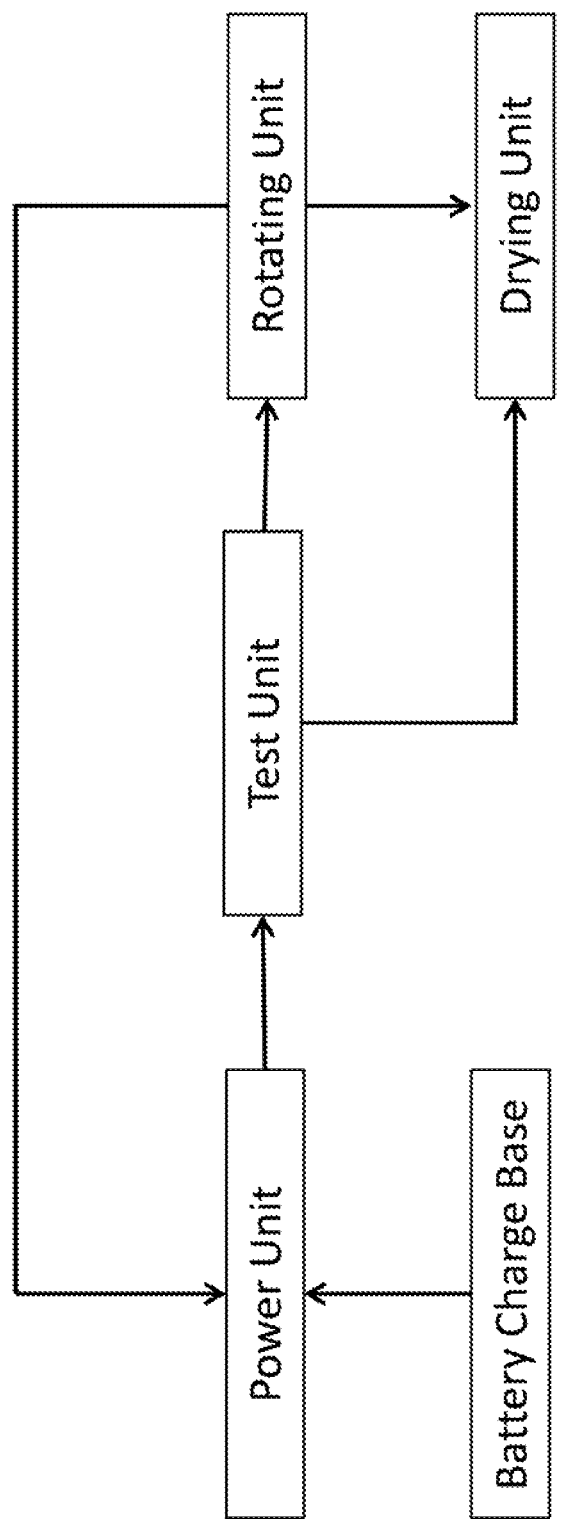
FIG. 1 is the schematic diagram of the smart folding toothbrush for the embodiment of this disclosure.
Figure 2:
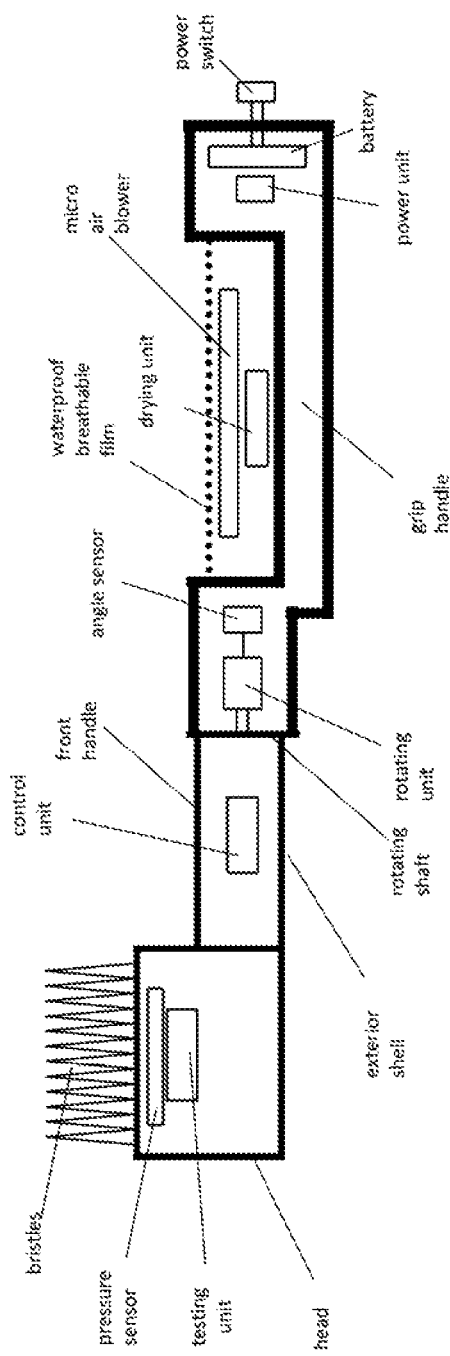
FIG. 2 is the structural diagram of the smart folding toothbrush for the embodiment of this disclosure.

A smart toothbrush of this disclosure includes a head, a front handle and a grip handle of the toothbrush. The head of the toothbrush has bristles. The exterior shell of the toothbrush is made of plastics. The front handle and the grip handle of the toothbrush are connected with a rotating shaft. See FIG. 2. It also includes a testing unit, a drying unit, a rotating unit, a power unit and a charging base. The power unit supplies power to the testing unit, drying unit and rotating unit. The testing unit controls the rotating unit and the drying unit. The rotating unit controls the drying unit and the power unit. See FIG. 1.

The testing unit is set inside the head of the toothbrush to test pressure and includes a pressure sensor. A first pressure threshold and a second threshold are preset. The second pressure threshold is higher than the first pressure threshold. When test pressure ranges between the first pressure threshold and the second pressure threshold, a first rotating signal is sent to the rotating unit; when test pressure is higher than the second pressure threshold, a second rotating signal is sent to the rotating unit.

Figure 3:
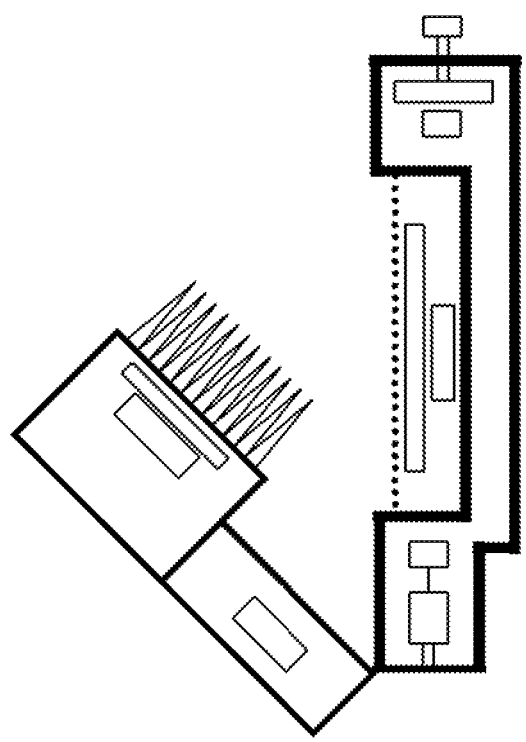
FIG. 3 is the structural diagram of the smart folding toothbrush for the embodiment of this disclosure where the rotating angle of the rotating shaft is 45°.
Figure 4:
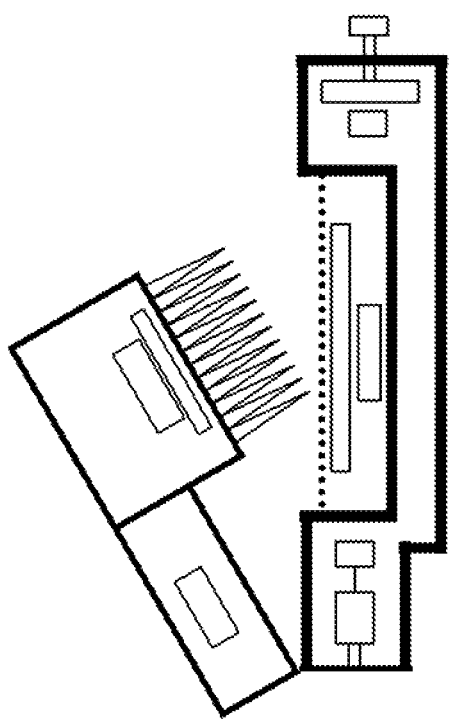
FIG. 4 is the structural diagram of the smart folding toothbrush for the embodiment of this disclosure where the rotating angle of the rotating shaft is 30°.

The rotating unit is set inside the front handle of the toothbrush, it is connected to the rotating shaft to control the rotating angle of the rotating shaft. Three angles of the rotating shaft are preset. The angles are respectively 180°, 45° and 30° as the angle between the drying unit and the toothbrush bristles. See FIGS. 2, 3, and 4. When the angle is 180°, the front handle and the grip handle of the toothbrush are on the same line, in other words, the toothbrush works normally, when the angle is 45° or 30°, the toothbrush bristles are dry.

The rotating unit includes an angle sensor, controlling the angle of the rotating shaft to 45° after receiving the first rotating signal and controlling the angle of the rotating shaft to 30° after receiving the second rotating signal. See FIGS. 3 and 4. Based on a pressure value detected by the testing unit and the water volume of the toothbrush bristles, the rotating angle of the front handle of the toothbrush is controlled. If there is a high water volume, the angle between the drying unit and toothbrush bristles is 30°, if there is a low water volume, the angle between the drying unit and toothbrush bristles is 45°. After the corresponding angle is achieved, a drying signal is sent to the drying unit.

The drying unit is set inside a rectangular groove below the grip handle of the toothbrush. Waterproof breathable film is set on the surface of this rectangular groove, linked to the exterior shell of the toothbrush in leak-tight manner to block entry of water into the groove and to ensure air permeability. This drying unit includes a micro air blower for drying the toothbrush bristles. After receiving drying signals of the rotating unit, the micro air blower starts blowing by sending out air via waterproof breathable film to the toothbrush bristles.

The drying, unit begins blowing and the testing unit detects when the pressure of toothbrush head is lower than the first pressure threshold. After the toothbrush bristles are dry, the testing unit sends a reset signal and a stop-drying signal to the rotating unit and the drying unit simultaneously.

After the rotating unit receives reset signal, it controls the angle of rotating shaft to 180°, i.e., the nominal working conditions, and sends a circuit disconnection signal to the power unit after completing rotation.

After receiving the testing unit's stop-drying signal, the drying unit stops blowing air.

The power unit is set on the top of the grip handle of the toothbrush and includes a battery and a power switch. The power switch is set on the side of the grip handle of the toothbrush to supply power to the testing unit, drying unit and control unit, and also receives rotating unit's circuit disconnection signals to disconnect circuit. The smart toothbrush, of this disclosure also includes a charging base. The smart toothbrush may be vertically placed on the charging base to provide power from the power unit.

Regarding the smart folding toothbrush of this disclosure, after using the toothbrush, the user simply turns on the power switch on the side of the grip handle of the toothbrush and puts the toothbrush onto the charge base to dry toothbrush bristles automatically. The toothbrush rotates to, the applicable angle based on tested pressure of the toothbrush-'head and water volume of toothbrush bristles. Then, the micro air blower starts blowing. Air is sent out via such waterproof breathable film to toothbrush bristles. Air blowing stops after the toothbrush bristles become dry. The front handle of the toothbrush is reset to the nominal working conditions of the toothbrush and power is disconnected. The process is automatic. The toothbrush bristles may be quickly blown dry and then automatically reset for convenience of further use to ensure dryness of toothbrush bristles to reduce bacteria for easy use.

The specification shows and describes embodiments of this disclosure. It should be understood that the disclosed device is not limited to the form that this article discloses, and it should not be deemed exclusive of any other embodiment. Instead it may be applied to various combinations, revisions and environments, and it can be altered with the above-mentioned instructions, techniques or knowledge of relevant fields within the scope of the disclosed device and concepts described by this article. No alteration or change carried out by professionals of this field shall deviate front the spirit and scope of this disclosure, and should fall under the protection of the claims attached to this invention.

What is claimed is:

1. A smart toothbrush, comprising:
   a head, wherein the head has bristles;
   a front handle; and
   a grip handle and the front handle are connected by a rotating shaft, which is characterized by a rotating unit inside the front handle, connected to the rotating shaft to control a rotating angle of the rotating shaft;
   a drying unit is located in the grip handle within a groove;
   a waterproof breathable film is set on a surface of the groove and is linked to an exterior shell of the smart toothbrush in a leak-tight manner to dry the bristles of the smart toothbrush;
   a testing unit is located inside the head of the smart toothbrush to test pressure, the testing unit comprises a pressure sensor having a first pressure threshold that is preset and a second pressure threshold that is preset, wherein the second pressure threshold is higher than the first pressure threshold, if the test pressure is between the first pressure threshold and the second pressure threshold, a first rotating signal is send to the rotating unit; if the test pressure is higher than the second pressure threshold, a second rotating signal is sent to the rotating unit; if the test pressure is lower than the first pressure threshold, a reset signal and a stop-drying signal ere sent the rotating unit and the drying unit simultaneously; and
   a power unit set is located on a top of the grip handle of the smart toothbrush and comprises a battery and a power switch;
   wherein the power switch is located on a side of the grip handle of the smart toothbrush to supply power to the testing unit, the drying unit and a control unit; and
   wherein the smart toothbrush is adapted to sit vertically on a charge base for power charging by the power unit.

2. The smart toothbrush of claim 1, characterized by the rotating unit having an angle sensor that receives the first rotating signal and controls the rotating angle of the rotating shaft to 45°, receives the second rotating signal and controls the rotating angle of the rotating shaft to 30° to send the stop-drying signal to the drying unit after a corresponding angle value is achieved.

3. The smart toothbrush of claim 1, characterized by the drying unit which comprises micro air blower that receives the stop-drying signal to initiate micro air blowing.

4. The smart toothbrush of claim 2, characterized by the drying unit which comprises micro air blower that receives the stop-drying signal to initiate micro air blowing.

5. The smart toothbrush of claim 1, characterized by the rotating unit that receives the reset signal to control the rotating angle of the rotating shaft to 180° before sending a circuit disconnection signal to the power unit.

6. The smart toothbrush of claim 2, characterized by the rotating unit that receives the reset signal to control the rotating angle of the rotating shaft to 180° before sending a circuit disconnection signal to the power unit.

7. The smart toothbrush of claim 3, characterized by the rotating unit that receives the reset signal to control the rotating angle of the rotating shaft to 180° before sending a circuit disconnection signal to the power unit.

8. The smart toothbrush of claim 4, characterized by the rotating unit that receives the reset signal to control the rotating angle of the rotating shaft to 180° before sending a circuit disconnection signal to the power unit.

9. The smart toothbrush of claim 1, characterized by the drying unit that receives the stop-drying signal, to terminate micro air blowing.

10. The smart toothbrush of claim 2, characterized by the drying unit that receives the stop-drying signal to terminate micro air blowing.

11. The smart toothbrush of claim 3, characterized by the drying unit that receives the stop-drying signal to terminate micro air blowing.

12. The smart toothbrush of claim 4, characterized by the drying unit that receives the stop-drying signal to terminate micro air blowing.

13. The smart toothbrush of claim 5, characterized by the drying unit that receives the stop-drying signal to terminate micro air blowing.

14. The smart toothbrush of claim 6, characterized by the drying unit that receives the stop-drying signal to terminate micro air blowing.

15. The smart toothbrush of claim 7, characterized by the drying unit that receives the stop-drying signal to terminate micro air blowing.

16. The smart toothbrush of claim 8, characterized by the drying unit that receives the stop-drying signal to terminate micro air blowing.

17. The smart toothbrush of claim 5, characterized by the power unit that receives the circuit disconnection signal to disconnect the power unit.

18. The smart toothbrush of claim 6, characterized by the power unit that receives the circuit disconnection to disconnect the power unit.

19. The smart toothbrush of claim 7, characterized by the power unit that receives the circuit disconnection signal to disconnect the power unit.

20. The smart toothbrush of claim 8, characterized by the power unit that receives the circuit disconnection signal to disconnect the power unit.

* * * * *